United States Patent
Kumar et al.

(10) Patent No.: US 11,331,324 B2
(45) Date of Patent: May 17, 2022

(54) MODIFIED RELEASE SUSPENSION OF ESLICARBAZEPINE

(71) Applicant: Jubilant Generics Limited, Noida (IN)

(72) Inventors: Dinesh Kumar, Noida (IN); Saurabh Srivastava, Noida (IN); Indranil Nandi, Yardley, PA (US); Rakesh K. Singh, Noida (IN); Amit Jha, Noida (IN); Kamal S. Mehta, Noida (IN)

(73) Assignee: Jubilant Generics Limited

( * ) Notice: Subject to any disclaimer, the term of this patent is extended or adjusted under 35 U.S.C. 154(b) by 67 days.

(21) Appl. No.: 16/828,858

(22) Filed: Mar. 24, 2020

(65) Prior Publication Data

US 2020/0222421 A1   Jul. 16, 2020

Related U.S. Application Data

(63) Continuation-in-part of application No. PCT/IB2018/057398, filed on Sep. 25, 2018.

(30) Foreign Application Priority Data

Sep. 25, 2017   (IN) .............................. 201711033832

(51) Int. Cl.
    *A61K 31/55*  (2006.01)
    *A61K 9/00*   (2006.01)
    *A61K 9/16*   (2006.01)

(52) U.S. Cl.
    CPC .............. *A61K 31/55* (2013.01); *A61K 9/009* (2013.01); *A61K 9/1694* (2013.01)

(58) Field of Classification Search
    CPC ....... A61K 31/55; A61K 9/009; A61K 9/1694
    See application file for complete search history.

(56) References Cited

U.S. PATENT DOCUMENTS

| | | | |
|---|---|---|---|
| 2003/0191192 A1 | 10/2003 | Venus | |
| 2010/0297181 A1* | 11/2010 | Hanada | ................... A61P 43/00 424/239.1 |
| 2013/0040939 A1* | 2/2013 | Vasconcelos | .......... A61K 31/55 514/217 |

FOREIGN PATENT DOCUMENTS

WO   2012091593 A1   7/2012

OTHER PUBLICATIONS

Trojer et al. Physical Chemistry chemical physics 15(41)2013) 17707-18302.*

* cited by examiner

*Primary Examiner* — Shirley V Gembeh

(74) *Attorney, Agent, or Firm* — William D. Hare, Esq.; McNeely, Hare & War, LLP

(57) ABSTRACT

The present invention discloses an extended release oral liquid pharmaceutical composition comprising eslicarbazepine or its pharmaceutically acceptable esters, salts, solvates, polymorphs, enantiomers or mixtures thereof in a pharmaceutically acceptable carrier. The extended release liquid compositions are in the form of ready-to-use liquid compositions or reconstituted liquid compositions. It also relates to processes for the preparation of said extended release liquid compositions. The prior art discloses immediate release oral liquid dosage form. The prepared novel test formulations exhibited desired pharmaceutical technical attributes.

19 Claims, No Drawings

MODIFIED RELEASE SUSPENSION OF ESLICARBAZEPINE

This is a continuation-in-part of International Application PCT/IN2018/057398, with a filing date of Sep. 25, 2018, which claims priority to Indian Application No. 201711033832, with a filing date of Sep. 25, 2017.

FIELD OF THE INVENTION

The present invention relates to orally administered modified release liquid pharmaceutical compositions of eslicarbazepine. The modified release liquid compositions are in the form of ready to use suspension or suspension powder for reconstitution. It also relates to the processes for the preparation of said liquid compositions.

BACKGROUND OF THE INVENTION

Eslicarbazepine acetate is used as an anticonvulsant drug. It is chemically known as (S)-10-acetoxy-10,11-dihydro-5H-dibenz[b,f]azepine-5-carboxamide. It is recommended for conditions such as epilepsy, affective disorders, and pain disorders. Eslicarbazepine is marketed in the United States as an immediate release tablet in of 200 mg, 400 mg, 600 mg and 800 mg strengths under the brand name Aptiom® by Sunovion Pharmaceuticals.

The tablet dosage form of Eslicarbazepine has a large tablet size and weight. Difficulty in swallowing large tablets and capsules is a problem for many patients and can lead to a variety of adverse events as well as induce significant non-compliance with the prescribed treatment regimens. Children, adolescents, and the elderly are particularly vulnerable population groups that are more likely than adults to experience difficulty in swallowing large tablets or capsules. The liquid dosage forms formulation design with an objective to minimize swallowing difficulties is likely to improve patient compliance by reducing dysphagia-related adverse events due to large tablet size and accordingly providing a more convenient and less cumbersome posology.

There exists a need in the art for liquid compositions of eslicarbazepine which provide ease administration, dose adjustment, and enhanced patient compliance.

U.S. Publication No. 2013/0040939 discloses an immediate release oral suspension formulation of eslicarbazepine comprising xanthan gum as a suspending agent and polyoxyethylene stearate as a wetting agent.

The prior art discloses only immediate release oral suspension of eslicarbazepine. There exists a need in the art for modified release liquid compositions of eslicarbazepine which are stable, provides ease of administration, dose adjustment, and enhanced patient compliance. Besides, the liquid compositions should be stable in terms of dissolution, viscosity, pH, sedimentation, phase separation and content uniformity.

Extended-release products offer potential benefits like, sustained blood levels, attenuation of adverse effects and improved patient compliance as dosing frequency is reduced. In case of anti-epileptic drugs extended-release dosage forms provide the convenience of once daily dosing with expected improvement in patient compliance, an improved tolerability profile resulting from lower peak plasma levels, and a better seizure control from fewer fluctuations in the plasma levels.

The modified release liquid compositions exhibit desirable technical attributes. The present invention provides modified release liquid compositions of eslicarbazepine which are ready to use suspension and suspension powder for reconstitution.

OBJECTS AND SUMMARY OF THE INVENTION

The present invention relates to orally administered modified release liquid pharmaceutical compositions of eslicarbazepine. The modified release liquid compositions are in the form of ready to use suspension or suspension powder for reconstitution. The liquid compositions offer better patient compliance and dosing flexibility based on age and body weight of the patients. It also relates to the processes for the preparation of said liquid compositions.

It is a principal object of the present invention provide a stable pharmaceutical composition comprising an anticonvulsant drug with one or more pharmaceutically acceptable excipients and/or carriers and processes for its preparation.

It is another object of the present invention to provide a stable modified release pharmaceutical composition in the form of a suspension comprising eslicarbazepine or its pharmaceutically acceptable esters, salts, solvates, polymorphs, enantiomers or mixtures thereof with one or more pharmaceutically acceptable excipients and/or carriers and processes for their preparation. The modified release suspension is in the form of ready to use suspension and suspension powder for reconstitution.

It is another object of the present invention to provide an oral modified release pharmaceutical composition in the form of a suspension comprising eslicarbazepine or its pharmaceutically acceptable esters, salts, solvates, polymorphs, enantiomers or mixtures thereof with one or more pharmaceutically acceptable excipients and/or carriers wherein the pharmaceutically acceptable excipient is selected from the group consisting of suspending agent, antioxidants, anticaking agent, antifoaming agent, pH adjusting agent, coloring agent, sweetening agent, flavouring agent, surfactant/solubilizer/wetting agent, gel forming agent, release-controlling agent, buffer, diluent and preservative.

Another object of the present invention is to develop a modified release suspension comprising eslicarbazepine or its pharmaceutically acceptable esters, salts, solvates, polymorphs, enantiomers or mixtures thereof by a manufacturing process which is consistent and therefore feasible for industrial production, while maintaining the stability.

The following embodiments further describe the objects of the present invention in accordance with the best mode of practice, however, the disclosed invention is not restricted to the particular embodiments hereinafter described.

In accordance with one embodiment of the present invention, there is provided a modified release dry powder for suspension comprising eslicarbazepine or its pharmaceutically acceptable esters, salts, solvates, polymorphs, enantiomers or mixtures thereof and at least one or more pharmaceutically acceptable excipients and/or carriers wherein the pharmaceutically acceptable excipient is selected from the group consisting of suspending agent/thickening agent/viscosity agent, antioxidant, anticaking agent, antifoaming agent, pH adjusting agent, coloring agent, sweetening agent, flavouring agent, solubilizer/wetting agent, gel forming agent, release-controlling agent, buffer, diluent and preservative.

In accordance with one embodiment of the present invention, there is provided a modified release ready to use stable liquid suspension comprising eslicarbazepine or its pharmaceutically acceptable esters, salts, solvates, polymorphs, enantiomers or mixtures thereof and at least one or more pharmaceutically acceptable excipients and/or carriers wherein the pharmaceutically acceptable excipient is selected from the group consisting of suspending agent/ thickening agent/viscosity agent, antioxidant, anticaking agent, antifoaming agent, adjusting agent, coloring agent, sweetening agent, flavouring agent, solubilizer/wetting agent, buffer, gel forming agent, release-controlling agent, diluent and preservative.

In accordance with another embodiment of the present invention, there is provided modified release dry powder for suspension compositions suitable for use as a liquid suspension for children or elderly patients. The compositions include eslicarbazepine or its pharmaceutically acceptable esters, salts, solvates, polymorphs, enantiomers or mixtures thereof and pharmaceutically acceptable excipients selected from the group consisting of suspending agents, viscosity enhancers, coating agents, preservatives, flavouring agents, thickening agent/viscosity agent, sweeteners, lubricants, wetting agents, gel forming agent, release-controlling agent, surfactants, buffering agents, and diluents.

In accordance with still another embodiment of the present invention, there is provided a process for the preparation of a stable modified release pharmaceutical composition in the form of a suspension comprising eslicarbazepine or its pharmaceutically acceptable esters, salts, solvates, polymorphs, enantiomers or mixtures thereof, wherein eslicarbazepine or its pharmaceutically acceptable esters, salts, solvates, polymorphs, enantiomers or mixtures thereof, wherein the liquid carrier is an aqueous and/or non-aqueous carrier.

In accordance with still another embodiment of the present invention, there is provided a process for the preparation of a stable modified release pharmaceutical composition in the form of a suspension comprising eslicarbazepine or its pharmaceutically acceptable esters, salts, solvates, polymorphs, enantiomers or mixtures thereof, wherein eslicarbazepine or its pharmaceutically acceptable esters, salts, solvates, polymorphs, enantiomers or mixtures thereof is in micronized form.

In accordance with still another embodiment of the present invention, there is provided a process for the preparation of a ready to use modified release liquid suspension of eslicarbazepine or its pharmaceutically acceptable esters, salts, solvates, polymorphs, enantiomers or mixtures thereof, comprising combining various components using conventional equipment such as overhead stirrers, ultrasonifiers, mills and homogenizers. Many different orders of adding components for mixing can be employed. The pH of the suspension is adjusted to a desired value using aqueous buffering agents as needed.

In accordance with still another embodiment of the present invention, there is provided a process for the preparation of a modified release dry powder for suspension composition of eslicarbazepine or its pharmaceutically acceptable esters, salts, solvates, polymorphs, enantiomers or mixtures thereof, which is suitable for suspension in water and/or water miscible suitable solvents to form an orally administrable product which comprises admixing modified release eslicarbazepine granules/pellets/beads with substantially dry pharmaceutically acceptable excipients selected from the group consisting of suspending agents/viscosity enhancers, coating agents, preservatives, flavouring agents, sweeteners, lubricants, surfactants/wetting agents, gel forming agents, buffering agents, and diluents to form a dry admixture, and transferring the dry admixture to a sealable storage container. In accordance with still another embodiment of the present invention, there is provided a stable modified release pharmaceutical composition in the form of a suspension comprising eslicarbazepine or its pharmaceutically acceptable esters, salts, solvates, polymorphs, enantiomers or mixtures thereof, wherein the composition is substantially free from other polymorphic forms.

In accordance with still another embodiment of the present invention, there is provided a stable modified release pharmaceutical composition in the form of a suspension comprising eslicarbazepine or its pharmaceutically acceptable esters, salts, solvates, polymorphs, enantiomers or mixtures thereof, in an amount of about 0.01% to about 90% by weight wherein, the composition exhibits desirable technical attributes like release profile, pourability, viscosity, dissolution, stability, re-suspendability and re-dispersibility and a process for preparing the same.

In accordance with still another embodiment of the present invention, there is provided a stable modified release pharmaceutical composition in the form of a suspension comprising eslicarbazepine or its pharmaceutically acceptable esters, salts, solvates, polymorphs, enantiomers or mixtures thereof, for the treatment of epilepsy, affective disorders, and pain disorders.

In accordance with still another embodiment of the present invention, there is provided a kit comprising:

(a) an extended release oral pharmaceutical suspension dosage form comprising eslicarbazepine or its salt thereof with one or more pharmaceutically acceptable excipients and/or carrier, (b) a dispensing and dosing syringe for administering the composition, and (c) optionally instructions for preparation and use.

DETAILED DESCRIPTION OF THE INVENTION

The present invention can be more readily understood by following the detailed description of the invention and a study of the included examples.

As used herein, the term "composition" or "formulation" or "dosage form", as in (pharmaceutical composition, is intended to encompass a drug product comprising an anticonvulsant or anti-epileptic drug, preferably eslicarbazepine or its pharmaceutically acceptable salts, esters, solvates, polymorphs, enantiomers or mixtures thereof, and other inert ingredient(s) (pharmaceutically acceptable excipients). Such pharmaceutical compositions are synonymous with "formulation" and "dosage form". Pharmaceutical compositions of the invention include, but are not limited to, modified release ready to use or powder for suspension/ suspension powder for reconstitution. The suspension powder for reconstitution comprises granules, pellets, or beads.

As used herein, the term "ready to use suspension" means a pre-constituted suspension which can be administered as such. The "powder for suspension" or "dry suspension" needs to be reconstituted with a liquid carrier to form a suspension.

As used herein, the term "Eslicarbazepine" is used in broad sense to include not only "Eslicarbazepine" per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable isomers, pharmaceutically acceptable polymorphs, pharmaceutically acceptable prodrugs thereof, and also its various crystalline and amorphous forms. In particular, the salt of eslicarbazepine is eslicarbazepine acetate. The term "Eslicarbazepine acetate" used in this specification means the S-isomer in substantially pure form, i.e. at least about 98% pure. The composition of the present invention comprises eslicarbazepine in an amount from about 0.01% w/w to about 90% w/w of the total composition, particularly in an amount from about 0.01% to about 30% w/w of the total composition.

The term "modified release" as used herein, refers to a release profile to effect delivery of eslicarbazepine over an extended period of time, as being between about 1 hour to about 2, 4, 6, 8, 12 hours. Modified release includes extended release, sustained release, controlled release, multiphase release, delayed release, pulsatile release, chrono release and the like. A modified release composition is one for which the drug release characteristics of time course and/or location are chosen to accomplish therapeutic or convenience objectives not offered by conventional dosage forms such as solutions or promptly dissolving dosage forms immediate release tablets.

The term immediate release, as used herein, implies that eslicarbazepine is released from the composition in an immediate release fashion, but may include taste-masking. When present in immediate release form, eslicarbazepine may be present as powder, pellets, granules, beads, and the like.

The term "inert particle," as used herein, refers to a particle made from a sugar sphere also known as a nonpareil seed, a microcrystalline cellulose sphere, a dibasic calcium phosphate head, a mannitol bead, a silica bead, a tartaric acid pellet, a wax based pellet, and the like.

The term "excipient" means a pharmacologically inactive component such as a thickening agent, viscosity agent, anticaking agent, antifoaming agent, pH adjusting agent, antioxidant, sweetening agent, flavoring agent, solubilizer/wetting agent, gel forming agent, rate-controlling agent, buffer, and preservative and the like. The excipients used in preparing the liquid pharmaceutical composition are safe and non-toxic. Reference to an excipient includes both one and more than one such excipient. Co-processed excipients are also covered under the scope of the present invention. Further, excipients may be in the form of powders or in the form of a dispersion. A combination of excipients performing the same function may also be used to achieve desired formulation characteristics. In addition to the aforementioned components, the eslicarbazepine oral suspension form can also optionally contain other excipients commonly found in pharmaceutical compositions such as alternative solvents, taste-masking agents, antioxidants, fillers, acidifiers, enzyme inhibitors and other components as described in Handbook of Pharmaceutical Excipients, Rowe et al., Eds., 6th Edition, Pharmaceutical Press (2009).

As used herein, the term "about" means±approximately 20% of the indicated value, such that "about 10 percent" indicates approximately 08 to 12 percent.

As used in this specification, the singular forms "a", and "the" include plural references unless the context clearly dictates otherwise. Thus, for example, a reference to "a process" includes one or more process, and/or steps of the type described herein and/or which will become apparent to those persons skilled in the art upon reading this disclosure and so forth.

The term "stable," as used herein, refers to chemical stability, wherein not more than 5% w/w of total related substances are formed on storage at 40° C. and 75% relative humidity (R.H.) or at 25° C. and 60% for a period of at least one month, particularly for a period of two months, and more particularly for a period of at least three months.

Unless otherwise stated, the weight percentages expressed herein are based on the final weight of the composition or formulation.

The present invention is a stable modified release liquid pharmaceutical composition of eslicarbazepine or its pharmaceutically acceptable salts.

The present invention is a stable pharmaceutical composition directed to ready to use oral modified release liquid suspension or modified release dry powder for suspension compositions suitable for use as a liquid suspension for administration to a subject in need thereof which comprises eslicarbazepine or its pharmaceutically acceptable salts.

In accordance with one embodiment, there is provided a stable pharmaceutical composition in the form of a modified release suspension comprising:
  (i) a core comprising eslicarbazepine; and
  (ii) at least one or more pharmaceutically acceptable excipients;
  (iii) a coating layer over said core comprising one or more release-controlling polymers.

In accordance with one embodiment, there is provided a stable pharmaceutical composition in the form of a modified release suspension comprising eslicarbazepine or its pharmaceutically acceptable salts with one or more pharmaceutically acceptable excipient and/or liquid carrier and process for its preparation Another embodiment of the present invention provides a modified release liquid pharmaceutical composition of eslicarbazepine or its pharmaceutically acceptable salt, ester, hydrate or polymorph thereof with one or more pharmaceutically acceptable excipients comprising:
  (i) modified release cores of eslicarbazepine comprising a release-controlling agent; and
  (ii) a pharmaceutically acceptable carrier.

According to another embodiment the present invention relates to the release-controlling agent may be present in the core or coated over the core or both.

According to another embodiment the present invention relates to the modified release core is prepared by extrusion-spheronization technique.

According to another embodiment the present invention relates to the modified release liquid pharmaceutical composition of eslicarbazepine comprising:
  (i) cores of eslicarbazepine coated with a release-controlling agent to form the modified release cores; and
  (ii) a pharmaceutically acceptable carrier.

According to one embodiment of the present invention relates to the modified release core is coated with a gel forming agent. Alternatively, inert particles are coated with a gel forming agent. Upon admixing with an aqueous medium a viscous suspension is formed suitable for oral administration.

In accordance another embodiment of present invention, there is provided a stable modified release suspension comprising eslicarbazepine or its pharmaceutically acceptable salts and one or more pharmaceutically acceptable excipients and/or a liquid carrier, wherein the composition is substantially free of xanthan gum. In accordance another embodiment of present invention, there is provided a stable modified release suspension comprising eslicarbazepine or its pharmaceutically acceptable salts and one or more pharmaceutically acceptable excipients and/or a liquid carrier, wherein the composition is substantially free of polyoxyethylene stearate.

In accordance with another embodiment of the present invention, there is provided a stable modified release suspension comprising eslicarbazepine or its pharmaceutically acceptable salts and one or more pharmaceutically acceptable excipients and/or a liquid carrier, wherein the composition is substantially free of xanthan gum and polyoxyethylene stearate.

According to one embodiment of the present invention which relates to the modified release liquid composition, the invention is a suspension of eslicarbazepine.

According to one embodiment of the present invention which relates to the modified release suspension, the invention is a ready to use suspension or suspension powder for reconstitution.

According to one embodiment of the present invention relates to the modified release suspension is an aqueous suspension.

Another embodiment of the present invention relates to a modified release oral pharmaceutical suspension dosage form of eslicarbazepine or its pharmaceutically acceptable salt, ester, hydrate or polymorph thereof with one or more pharmaceutically acceptable excipients comprising:
 a) core comprising eslicarbazepine;
 b) a release-controlling agent;
 c) a suspending agent;
 d) a diluent;
 e) a preservative;
 f) optionally an antioxidant;
 g) pH adjusting agent in sufficient amounts to maintain the pH of the composition in t range of about 3.0 to about 8.0; and/or a pharmaceutically acceptable liquid carrier.

Another embodiment of the present invention relates to a multiparticulate based pharmaceutical composition comprising
 a) a core comprising eslicarbazepine or its pharmaceutically acceptable esters, salts, solvates, polymorphs, enantiomers or mixtures thereof and one or more pharmaceutically acceptable excipients;
 b) coated with one or more rate controlling agent; and
 c) optionally mixing the coated core with one or more excipients selected from the group of a diluent/carrier, buffering agent, suspending/thickening agent, sweeteners, flavouring agent, stabilizing agent, preservatives and mixtures thereof,
 wherein the composition is substantially free of xanthan gum and/or polyoxyethylene stearate.

Another embodiment of the present invention relates to a multiparticulate based pharmaceutical composition comprising: a) an inert core comprising mannitol or Microcrystalline cellulose; b) drug layer comprising eslicarbazepine or its pharmaceutically acceptable esters, salts, solvates, polymorphs, enantiomers or mixtures thereof and one or more pharmaceutically acceptable excipients; c) coated with one or more rate controlling agent; and d) optionally mixing the coated core with one or more excipients selected from the group of a diluent/carrier, buffering agent, suspending/thickening agent, sweeteners, flavouring agent, stabilizing agent, preservatives and mixtures thereof, wherein the composition is substantially free of xanthan gum and/or polyoxyethylene stearate.

In yet another embodiment of the present invention, multiparticulate system based composition of eslicarbazepine or its pharmaceutically acceptable esters, salts, solvates, polymorphs, enantiomers or mixtures thereof is in the form of Powder for oral suspension.

According to one embodiment of the present invention relates to the modified release suspension has a pH in a range of about 3.0-8.0.

According to another embodiment of the present invention, the amount of eslicarbazepine in the suspension ranges from about 0.1 mg/ml to about 400 mg/ml. The amount of eslicarbazepine in the suspension ranges preferably from about 0.5 mg/mL to 300 mg/mL, preferably from about 0.5 mg/ML to 200 mg/mL, preferably from about 0.5 mg/mL to 100 mg/mL. More preferably the amount of eslicarbazepine in the suspension ranges from about 0.5 mg/ML to 75 mg/mL. Particularly, the amount of eslicarbazepine in the suspension is 1 mg/mL, 2 mg/5 mL, 5 mg/5 mL, 25 mg/5 mL, 50 mg/5 mL, 100 mg/5 mL and 250 mg/5 mL, 5 mg/mL, 25 mg/mL, 50 mg/mL, 100 mg/mL and 250 mg/mL.

According to another embodiment of the present invention, the amount of eslicarbazepine in the suspension ranges from about 0.01% to about 90% by weight on the basis of the total weight of the suspension. Particularly, the amount of eslicarbazepine in the suspension ranges from about 0.01% to about 30% by weight on the basis of the total weight of the composition.

According to another embodiment of the present invention, the eslicarbazepine is layered onto an inert particle to form the core.

According to another embodiment of the present invention, the pharmaceutically acceptable carrier comprises one or more of pharmaceutically acceptable excipients selected from the group comprising one or more of viscosity agent, anticaking agent, antifoaming agent, pH adjusting agent, coloring agent, sweetening agent, flavoring agent, surfactant or wetting agent, gel forming agent, release controlling agent, buffer, diluent, preservative, and antioxidant.

According to another embodiment of the present invention, the modified release liquid pharmaceutical composition comprises an immediate release component.

According to another embodiment of the present invention, the modified release liquid pharmaceutical composition is administered once daily.

In accordance with another embodiment of the present invention, provides a process for the preparation of modified release liquid pharmaceutical composition of eslicarbazepine which is consistent and therefore feasible for industrial production, while maintaining stability and pharmaceutical equivalence to the reference formulation.

In accordance with another embodiment of the present invention, provides a method of treating a medical condition in a subject by administering a modified release liquid pharmaceutical composition of eslicarbazepine comprising eslicarbazepine and one or more pharmaceutically acceptable excipient and/or carrier.

In accordance with another embodiment of the present invention, the medical condition is selected from the group comprising epilepsy, neuropathic pain, migraine, fibromyalgia, trigeminal neuralgia, bipolar disorders, attention disorders, anxiety disorders, affective disorders, and schizoaffective disorders, sensorimotor disorders, and vestibular disorders.

In accordance with another embodiment of the present invention, the epilepsy is partial-onset seizures with or without secondary generalization, primary generalized seizures, and absence seizures. According to another embodiment of the above aspect, the composition further comprises one or more anticonvulsant drugs.

In accordance with one embodiment of the present invention, there is provided a stable pharmaceutical composition in the form of a modified release suspension comprising eslicarbazepine or its pharmaceutically acceptable salts with one or more pharmaceutically acceptable excipient and/or liquid carrier, wherein liquid carrier is selected from the group comprising aqueous and non-aqueous carrier. The aqueous carrier is selected from the group comprising water or a combination of water and a water-miscible organic solvent. The nonaqueous carrier is selected from the group comprising oils e.g., peanut oil, soy bean oil, corn oil, sesame oil, cottonseed oil, mineral oil, fatty acid esters, fatty acid esters of polyethylene glycols, glyceryl mono-oleate, ethyl oleate, acetylated glycerides, or combinations thereof.

In accordance with another embodiment of the present invention, there is provided a stable pharmaceutical composition in the form of a modified release suspension comprising eslicarbazepine or its pharmaceutically acceptable salts and/or a liquid carrier, wherein the sweetening agent is selected from the group sugar or a sugar alcohol such as sucrose, dextrose, sucralose, sorbitol, fructose, mannitol and invert sugar and sugar substitutes such as saccharin sodium, aspartame and combinations thereof.

In accordance with other embodiment of the present invention, there is provided a stable modified release suspension comprising eslicarbazepine or its pharmaceutically acceptable salts, wherein the suspension is a liquid suspension packaged in a bottle.

In accordance with yet another embodiment of the present invention, there is provided a stable modified release suspension comprising eslicarbazepine or its pharmaceutically acceptable salts, wherein the suspension is a powder for suspension packaged in a bottle or sachets.

In accordance with still another embodiment of the present invention, there is provided a kit comprising:

(a) an extended release oral pharmaceutical suspension dosage form comprising eslicarbazepine or its salt thereof with one or more pharmaceutically acceptable excipients and/or carrier, (b) a dispensing and/or dosing syringe for administering the composition, and (c) optionally instructions for preparation and use.

In accordance with still another embodiment of the present invention, there is provided a kit comprising:

an extended release oral pharmaceutical suspension dosage form comprising eslicarbazepine or its salt thereof with one or more pharmaceutically acceptable excipients and/or carrier, (b) a dispensing and/or dosing syringe or a measuring cup for administering the composition, and (c) optionally instructions for preparation and use.

In accordance with still another embodiment of the present invention, there is provided a kit comprising:

(a) an extended release oral pharmaceutical suspension dosage form comprising eslicarbazepine or its salt thereof with one or more pharmaceutically acceptable excipients and/or carrier, (b) a measuring cup for administering the composition, and (c) optionally instructions for preparation and use thereof.

According to another embodiment of the present invention, eslicarbazepine has a particle size distribution $D_{90}$ less than about 200 µm eslicarbazepine has a particle size distribution $D_{90}$ between 5 µm and 200 µm. Eslicarbazepine has a particle size distribution particularly $D_{90}$ between 5 µm and 175 µm, particularly $D_{90}$ between 5 µm and 150 µm, particularly $D_{90}$ between 5 µm and 125 µm, particularly $D_{90}$ between 5 µm and 100 µm and particularly $D_{90}$ between 5 µm and 75 µm. The eslicarbazepine coated core may be further optionally coated with a coating layer comprising a film-forming agent to mask the bitter taste or to improve the stability. The coating layer prevents eslicarbazepine release during storage, but is quickly penetrated by gastric fluid allowing rapid release of eslicarbazepine. In one instance, the film-forming agent can have a pH dependent solubility in which the release of active ingredient is prevented by using a pre-adjusted pH of the liquid composition such that the film-forming agent does not get dissolved in the liquid composition but get dissolved when exposed to the physiological conditions.

The term "gel forming agent", as used herein, refers to various gelling and viscosity agents, thickeners, solution binders, and/or emulsifiers. The gel forming agent increases the viscosity of the aqueous medium.

The modified release liquid compositions include ready to use oral suspension and suspension powder for reconstitution. The suspension powder for reconstitution can be in the form of powder, granules, pellets, beads, spheroids, multi-particulates, and the like. The suspension powder for reconstitution are finally reconstituted to modified release suspension/dispersion before administration such as by dispersing it a suitable pharmaceutically acceptable carrier/vehicle.

The pharmaceutically acceptable excipients used in the preparation of modified release suspension may comprise a suspending/viscosity agent, anticaking agent, antifoaming agent, pH adjusting agent, coloring agent, sweetening agent, flavoring agent, surfactant/wetting agent, buffer, diluent, preservative, antioxidant, release-controlling agent, and combinations thereof.

The viscosity agent/suspending agent enhances the physical stability of the composition by sufficiently increasing the viscosity so as to retard the settling rate, yet allowing adequate pourability. They also allow the product to be easily resuspendable so that an appropriate dose can be delivered with minimal shaking. Suitable thickening agents/viscosity agents/suspending agents are selected from the group comprising cellulose derivatives such as hydroxyethyl cellulose, hydroxypropyl cellulose, hydroxypropylmethyl cellulose, methylcellulose, carboxymethyl cellulose and its salts/derivatives e.g., carboxymethyl cellulose sodium (sodium CMC), microcrystalline cellulose, and co-processed spray dried forms of microcrystalline cellulose and carboxymethyl cellulose sodium (such as Avicel® RC-501, Avicel® RC-581, Avicel® RC-591, and Avicel® CL-611), carbomers (such as those available under the trade name Carbopol), gums such as locust bean gum, tragacanth gum, arabinogalactan gum, agar gum, gellan gum, guar gum, apricot gum, karaya gum, sterculia gum, acacia gum, gum arabic, and carrageenan; pectin; propylene glycol alginate, dextran, gelatin, polyethylene glycols; polyvinyl compounds such as polyvinyl acetate, polyvinyl alcohol, and polyvinyl pyrrolidone, sugar alcohols such as xylitol and mannitol, colloidal silica, maltodextrin, starch, and mixtures thereof. The liquid compositions of the present invention are free of xanthan gum. The suspending agents/viscosity agents are present in an amount of about 0.05% to about 20% w/w of the composition. Particularly, the suspending agents are present in an amount of about 0.1% to about 10% w/w of the composition. More particularly, the suspending agents are present in an amount of about 0.1% to about 5% w/w of the composition. Much more particularly, the suspending agents are present in an amount of about 0.1% to about 3% w/w of the composition.

The suspension is easily pourable and when shaken has a viscosity in the range of 100 to 5000 cP at 25° C. Particularly, the viscosity is in the range of 100 to 2500 cP at 25° C. More particularly, the viscosity is in the range of 100 to 1500 cP at 25° C.

The term shaken as used herein refers to shaken prior to use, e.g. by a patient, e.g. vigorously shaken, e.g. by hand, e.g. for 5 to 60 seconds.

The viscosity can be measured by using as suitable instalment such as Brookfield viscometer, Haake VT 550 viscometer at room temperature (25° C.).

Suitable anti-caking agents are selected from the group comprising colloidal silicon dioxide, powdered cellulose, tribasic calcium phosphate, magnesium trisilicate, starch, or mixtures thereof. The anticaking agents are present in an amount of about 0.1% to about 10% w/w of the composition.

Suitable antifoaming agents are selected from the group comprising methylated linear siloxane polymers end blocked with trimethylsiloxyl units such as dimethicone and simethicone, as well as mixtures of dimethicone with an average chain length of 200 to 250 dimethylsiloxane units and silica gel.

The suspension of the present invention has a in a range of about 3.0-8.0. Particularly, the pH of suspension has a pH in the range of about 5.0-7.0. In order to maintain the desired pH range pH adjusting agents/buffering agents are added. Suitable pH adjusting agents/buffering agents are selected from the group comprising citric acid, sodium citrate, sodium phosphate, potassium citrate, gluconic acid, lactic acid, acetic acid, sodium gluconate, sodium lactate, acetate buffer, sodium acetate, potassium citrate, sodium bicarbonate, potassium bicarbonate, sodium dihydrogen phosphate and potassium dihydrogen phosphate, and combinations thereof.

Suitable coloring agent are selected from the group comprising FD&C(Federal Food, Drug and Cosmetic Act) approved coloring agents; natural coloring agents; natural juice concentrates; pigments such as iron oxide, titanium dioxide, and zinc oxide; and combinations thereof.

Suitable sweetening agent are selected from the group comprising saccharine or its salt, acesulfame or its salt, cyclamate or its salt, aspartame, neotame, alitame, sucralose, and stevioside.

Suitable flavoring agents are selected from the group comprising grape, cherry, citrus, peach, strawberry, raspberry, banana, bubble gum, peppermint, grapefruit, orange, lime, lemon, mandarin, pineapple, mango, passion fruit, kiwi, apple, pear, peach, apricot, banana, cranberry, blueberry, black currant, red currant, gooseberry, lingon berries, camille, valerian, spearmint, and combinations thereof.

Diluents or fillers are substances which usually provide bulk to the composition. Various useful fillers or diluents include, but are not limited to sucrose, sugar alcohols, sorbitol, xylitol, erythritol, starch, pregelatinized starch, calcium carbonate, calcium phosphate, dibasic anhydrous, calcium phosphate, dibasic dihydrate, calcium phosphate tribasic, calcium sulphate, cellulose powdered, silicified microcrystalline cellulose, cellulose acetate, lactose, magnesium carbonate, magnesium oxide, maltodextrin, mannitol, microcrystalline cellulose, polydextrose, sodium alginate, sodium chloride and or mixtures thereof. Preferably diluent used is sucrose. The diluent is present in an amount of about 5% w/w to about 85% w/w of the total composition.

Suitable surfactant or wetting agents are selected from the group comprising non-ionic, anionic, cationic, or zwitterionic surfactants, and combinations thereof. Suitable examples of wetting agents are sodium lauryl sulphate, cetrimide, polyethylene glycols; polyglycerin fatty acid esters such as decaglyceryl monolaurate and decaglyceryl monomyristate, sorbitan fatty acid esters such as sorbitan monostearate; polyoxyethylene sorbitan fatty acid ester such as polyoxyethylene sorbitan monooleate, polyoxyethylene alkyl ether such as polyoxyethylene lauryl ether, polyoxyethylene castor oil, polyoxyethylene-polyoxypropylene block copolymers such as poloxamers, and combinations thereof. Particularly, surfactant or wetting agents are non-ionic. The liquid compositions of the present invention are free of polyoxyethylene stearate such as polyoxy 100 stearate (Myrj® 59P) as wetting agent. The surfactant or wetting agents are present in an amount of about 0.01% to about 2% w/w of the composition.

Carrier/vehicle/solvent used in the suspension of the present invention include aqueous and non-aqueous carrier but are not limited to water, alcohol, polyethylene glycol, propylene glycol or glycerin buffers, oil, or combinations thereof. Particularly, the suspensions are aqueous based. By "aqueous carrier" is meant a suspension comprising water, or a combination of water and a water-miscible organic solvent or solvents. Water-miscible solvents include but are not limited to propylene glycol, polyethylene glycol and ethanol. By "non-aqueous carrier" is meant a suspension in which the carrier does not include water. The carrier can also include one more pharmaceutically acceptable excipients which can be in dissolved or dispersed form. The carrier is present in an amount from about 30 w/w % to about 95 w/w %, particularly from about 50 w/w % to about 95 w/w %.

Various useful preservatives include, but are not limited to, parabens such as methylparaben, propylparaben, butyl paraben and their salts, sorbic acid, sodium sorbate, potassium sorbate, calcium sorbate, benzoic acid, sodium benzoate, potassium benzoate, calcium benzoate, methyl hydroxybenzoate, ethyl para-hydroxybenzoate, sodium ethyl parahydroxybenzoate, sodium metabisulphite, chlorhexidine, diazolidinyl urea, sodium citrate, butylated hydroxyl toluene (BHT), butylated hydroxyl anisole (BHA), tocopherol, ethylenediamine tetraacetic acid, propyl gallate, quaternary compounds, e.g. benzalkonium chloride and cetylpyridinium chloride, phenyl ethyl alcohol and the like. In particular, the preservative is selected from benzoic acid and its salts and parabens. The preservative is present in an amount of about 0.001% w/w to about 3% w/w of the composition.

Suitable antioxidants are selected from the group comprising butylated hydroxytoluene (BHT), butylated hydroxyanisole (BHA), sodium metabisulfite, ascorbic acid, propyl gallate, thiourea, tocopherols, beta-carotene, and combinations thereof.

The release-controlling agent is selected from the group comprising a pH-dependent release-controlling agent, a pH-independent release-controlling agent, and mixtures thereof. The release-controlling agent is present in an amount of about 0.1% w/w to about 60% w/w of the composition. Particularly, the release-controlling agent is present particularly in an amount of about 0.1% w/w to about 30% w/w of the composition, particularly in an amount of about 0.1% w/w to about 20% w/w of the composition, particularly in an amount of about 0.1% w/w to about 10% w/w of the composition.

Suitable pH-dependent release-controlling agents e selected from the group comprising acrylic copolymers such as methacrylic acid and methyl methacrylate copolymers, e.g., Eudragit® L 100 and Eudragit® S 100, dimethylaminoethyl methacrylate and butyl methacrylate and methyl methacrylate copolymers e.g., Eudragit® E 100, Eudragit® E PO, methacrylic acid and ethyl acrylate copolymers, e.g., Eudragit® L100-55 and Eudragit® L30 D-55, methyl acrylate and methacrylic acid and octyl acrylate copolymers, styrene and acrylic acid copolymers, butyl acrylate and styrene and acrylic acid copolymers, and ethylacrylate-methacrylic acid copolymer; cellulose acetate phthalate; cellulose acetate succinates; hydroxyalkyl cellulose phthalates such as hydroxypropylmethyl cellulose phthalate: hydroxyalkyl cellulose acetate succinates such as hydroxypropylmethyl cellulose acetate succinate, vinyl acetate phthalates; vinyl acetate succinate; cellulose acetate trimellitate, polyvinyl derivatives such as polyvinyl acetate phthalate, polyvinyl alcohol phthalate, polyvinyl butylate phthalate, and polyvinyl acetoacetyl phthalate, zein, shellac, and mixtures thereof.

Suitable pH-independent release-controlling agents are selected from the group comprising cellulosic polymers such as methyl cellulose, hydroxyethyl cellulose, hydroxypropyl cellulose, hydroxyethylmethyl cellulose, hydroxypropylmethyl cellulose, cellulose acetate, ethyl cellulose, and carboxy methylcellulose; acrylic copolymers such as methacrylic acid copolymers, e.g., Eudragit® RS, Eudragit® RL, Eudragit® NE 30 D; gums e.g., guar gum, locust bean gum, tragacanth, carrageenan, alginic acid, gum acacia, gum arabic, gellan gum; triglycerides; polyethylene derivatives e.g., polyethylene glycol and polyethylene oxide; polyvinyl alcohol; polyvinyl acetate; waxes, e.g., glyceryl behenate (Compritol®), Lubritab®, and Gelucires® lipids; fatty acids or their salts/derivatives; polyvinyl polymers; a mixture of polyvinyl acetate and polyvinyl pyrrolidone, e.g., Kollidon® SR; and mixtures thereof.

Suitable binders are selected from the group comprising gums such as guar gum, acacia, alginic acid, sodium alginate; carbomers; dextrin; maltodextrin; celluloses e.g., methylcellulose, ethyl cellulose, hydroxyethyl cellulose, hydroxypropyl cellulose, hydroxypropylmethyl cellulose, hydroxyethylmethyl cellulose, carboxymethyl cellulose sodium; povidone; dextrose; polydextrose, starch, pregelatinized starch, microcrystalline cellulose, polymethacrylates including acrylic copolymers, gelatin, and mixture thereof. The binder is present in an amount of about 0.1% w/w to about 30% w/w of the composition.

Suitable disintegrants are selected from the group comprising carboxymethyl cellulose sodium, croscarmellose sodium, crospovidone, polacrilin potassium, sodium starch glycolate, alginic acid, sodium alginate, microcrystalline cellulose, silicified microcrystalline cellulose, guar gum, colloidal silicon dioxide, docusate sodium, low substituted hydroxypropyl cellulose, magnesium aluminum silicate, methyl cellulose, starch, pregelatinized starch, and combinations thereof. The disintegrant is present in an amount of about 0.1% w/w to about 20% w/w of the composition.

Suitable glidants are selected from the group comprising silica, calcium silicate, magnesium silicate, colloidal silicon dioxide, corn starch, talc, stearic acid, magnesium stearate, calcium stearate, sodium stearyl fumarate, hydrogenated vegetable, and mixtures thereof. The glidant is present in an amount of about 0.1% w/w to about 6% w/w of the composition.

In the pharmaceutical suspension of the present invention the average particle size of eslicarbazepine is less than about 300 µm, particularly less than 200 µm, more particularly less than 150 µm, and much more particularly less than 100 µm. The particle size of eslicarbazepine can be measured by suitable techniques such as laser light scattering (e.g. Malvern Light Scattering), coulter counter, microscopy, fraunhofer diffraction, and any other technique known in the art.

The cores of eslicarbazepine can be prepared by any method known in the art, e.g., extrusion-spheronization, wet granulation, dry granulation, hot-melt extrusion granulation, spray drying, and spray congealing. Alternatively, eslicarbazepine can be layered onto an inert particle to form the core.

Further, eslicarbazepine can be directly coated with a release-controlling agent to form the microparticles or microcapsules. The microparticles or microcapsules can be prepared by a process of homogenization, solvent evaporation, coacervation phase separation, spray drying, spray congealing, polymer precipitation, or supercritical fluid extraction. Alternatively, the modified release cores can be optionally mixed with one or more pharmaceutically acceptable excipients to form the suspension powder for reconstitution which can be reconstituted with a suitable pharmaceutically acceptable carrier/vehicle.

Powder/granules for oral suspension can be reconstituted using water or Powder/granules for oral suspension can be administered by sprinkling the powder/granules on one teaspoonful of applesauce or empty granules into a small cup or teaspoon containing one teaspoon of apple juice.

Modified release liquid composition of eslicarbazepine can be prepared by (i) preparing cores comprising eslicarbazepine and one or more pharmaceutically acceptable excipients; dissolving/dispersing a release-controlling agent and one or more pharmaceutically acceptable coating excipients in a suitable solvent; (iii) applying the coating composition of step (ii) over the cores of step (i); (iv) dissolving/dispersing one or more pharmaceutically acceptable excipients in a pharmaceutically acceptable vehicle to form a pharmaceutically acceptable carrier; and (v) dispersing the coated cores of step (iii) in the carrier of step (iv) to obtain the modified release liquid composition.

Alternatively, process for the preparing an extended release dosage force of eslicarbazepine, comprising the steps:

a) blending eslicarbazepine with one or more pharmaceutically acceptable excipients, b) granulating the blend, using a surfactant, c) further coating the granules of step (b) with a rate controlling agent, d) drying and lubricating the granules of step c), e) blending the granules with one or more pharmaceutically acceptable excipients, e) filling into suitable bottle/sachet/pouch.

Alternatively, the modified release coated cores can be optionally mixed with one or more pharmaceutically acceptable excipients to form the suspension powder for reconstitution which can be reconstituted with a suitable pharmaceutically acceptable carrier/vehicle.

Eslicarbazepine can also be present in complexed form with ion-exchange resins which are coated with a release-controlling agent to form the modified release core. The modified release cores are optionally mixed with one or more pharmaceutically acceptable excipients and dispersed in a pharmaceutically acceptable carrier to form ready to use modified release liquid composition. Alternatively, the modified release cores can be optionally mixed with one or more pharmaceutically acceptable excipients to form the suspension powder for reconstitution which can be reconstituted with a suitable pharmaceutically acceptable carrier/vehicle.

The modified release suspension can be packaged in a suitable pack such as bottle e.g., glass bottle, amber colored polyethylene terephthalate (PET) bottle, high density polyethylene (HDPE) bottle, low density polyethylene (LDPE) bottle, and polypropylene (PP) bottle, packet, pouch, and sachet.

The glass or plastic bottle is provided with a child proof closure. The package can include a syringe, dosing syringe or dispensing syringe or measuring cup or any combination (marked in mL) for ease of dosing. The container(s) of the present invention may have a syringe adapted to be attached to the container. The syringe or cup as per the present invention can be of material such as polyethylene terephthalate (PET), glass, high density polyethylene (HDPE), low density polyethylene (LDPE), polypropylene (PP) or any other material known in the art.

The compositions of the present invention are for oral administration. The compositions may be taken in measured doses using a container, cup, straw, spoon, syringe, dispensing syringe, dosing syringe or any other suitable device. The compositions may be provided in liquid form, or in dry form (such as granule or powder or multiparticulate) to which water or liquid solvent or diluent is added to provide a liquid composition of this invention. Ingredients suitable for liquid compositions are known and such compositions may be made by methods known in the art. In an embodiment, the syringe, dispensing syringe or dosing syringe or combination thereof are used to transfer a predetermined amount of the composition comprising eslicarbazepine or its salt thereof, into the patient's mouth. In an embodiment, the measuring cup is used to measure the dose as per patient's requirement so that a precise dosage can be obtained for oral administration.

The modified release suspensions of the present invention are homogenous and deliver the desired dose of eslicarbazepine in every use without any risk of overdosing or under dosing. The compositions provide predictable eslicarbazepine release throughout the shelf life.

The invention may be further illustrated by the following examples, which are for illustrative purposes only and should not be construed as limiting the scope of the invention in any way.

EXAMPLES 1-5 Suspension Powder for Reconstitution

| Ingredients | Quantity (% w/w) | | | | |
|---|---|---|---|---|---|
| Example | 1 | 2 | 3 | 4 | 5 |
| Eslicarbazepine | 11.44 | 11.44 | 11.44 | 11.44 | 11.44 |
| Microcrystalline cellulose | 3.43 | — | — | — | 1.71 |
| HPMC | — | 3.43 | 9.15 | 1.14 | 1.71 |
| Sucrose | 75.24 | 75.16 | 69.44 | 77.45 | 75.2 |
| Sodium CMC | 0.69 | 0.69 | 0.77 | 0.77 | 0.68 |
| Polysorbate 80 | — | 0.08 | — | — | — |
| Ethyl Cellulose | 9.15 | 9.15 | 9.15 | 9.15 | 9.15 |
| Banana Flavor | 0.2 | 0.2 | 0.2 | 0.2 | 0.2 |
| Cherry Flavor | 0.2 | 0.2 | 0.2 | 0.2 | 0.2 |
| Isopropyl Alcohol (for ethyl cellulose coating) | q.s. | q.s. | q.s. | q.s. | q.s. |
| Water (for granulation) | q.s. | q.s. | q.s. | q.s. | q.s. |

Procedure:
1) blended eslicarbazepine with HPMC, sodium CMC and sucrose (and microcrystalline cellulose, Examples 1 and 5);
2) granulated the blend, using water and optionally a surfactant (e.g., polysorbate 80, Example 2);
3) further granules of step 2 were coated with a rate controlling agent (e.g., ethyl cellulose);
4) granules of step 3 were dried;
5) granules of step 5 were blended with one or more pharm pharmaceutically acceptable excipients such as flavouring agents and sweetening agents; and
6) obtained granules were packed in a suitable bottle/sachet/pouch.

The suspension powder for reconstitution is reconstituted with vehicle/liquid carrier when required to form the modified release liquid composition.

Assay for Eslicarbazepine

The suspension powders for reconstitution of Examples 1-5 were analyzed for drug content by HPLC method using C18 column (150×4.6 mm, 5 μm) using acetonitrile: water (50:50) at 215 nm.

All the batches exhibit assay of at least 99%.

pH data: pH values were determined using potentiometry using USP <791>

TABLE 1

| pH Value | |
|---|---|
| Composition | pH |
| Example 1 | 6.10 |
| Example 2 | 6.90 |
| Example 3 | 7.15 |
| Example 4 | 6.70 |
| Example 5 | 6.80 |

Dissolution Studies

The powder for suspension of Example 2 was evaluated for in-vitro eslicarbazepine release. The in-vitro dissolution was determined using a USP type II apparatus at 50 rpm in 1000 mL of acetate buffer (pH 4.5) at 37±0.5° C. by HPLC method. The results are represented in Table 2.

TABLE 2

Percentage (%) of the In Vitro Eslicarbazepine Release in USP type II apparatus at 50 rpm in 1000 mL of acetate buffer (pH 4.5)

| Time (flour) | Percentage of Eslicarbazepine Release of Example 2 |
|---|---|
| 1 | 17 |
| 2 | 28 |
| 4 | 42 |
| 10 | 56 |
| 12 | 58 |

What is claimed:

1. An extended release powder for oral suspension of eslicarbazepine acetate comprising one or more cores and pharmaceutically acceptable excipients comprising:
   (i) the one or more cores comprising (a) 0.1% to about 40% by weight of eslicarbazepine acetate;
   (b) 0.1% to 10% by weight of suspending agent selected from carboxymethyl cellulose sodium, co-processed microcrystalline cellulose and carboxymethyl cellulose sodium, hydroxypropyl cellulose, hydroxypropylmethyl cellulose, methylcellulose, carbomer, gums, and combinations thereof;
   (c) 0% to 2% by weight of surfactant selected from sodium lauryl sulphate, polyethylene glycol, sorbitan fatty acid ester, polyoxyethylene sorbitan fatty acid ester, poloxamer, and combinations thereof;

(d) 5% to 85% by weight of diluent selected from the group consisting of sucrose, sorbitol, xylitol, erythritol, lactose, maltodextrin, mannitol, microcrystalline cellulose, polydextrose, and combinations thereof, and (ii) a coating layer over said core, the coating layer comprising 0.1% to 60% by weight of one or more release-controlling agents selected from the group consisting of ethyl cellulose, hydroxyethyl cellulose, hydroxypropylmethyl cellulose, methacrylic acid copolymer, glyceryl behenate, mixture of polyvinyl acetate and polyvinyl pyrrolidone, polyethylene oxide and combinations thereof;

wherein the powder for oral suspension is free of xanthan gum and polyoxyethylene stearate.

2. The extended release powder for oral suspension of claim 1, wherein the pharmaceutically acceptable excipient further comprises one or more of a pH adjusting agent, buffer, flavouring agent, sweetening agent and combinations thereof.

3. The extended release powder for oral suspension of claim 1, wherein the composition further comprises eslicarbazepine in an immediate release form.

4. The extended release powder for oral suspension of claim 1, wherein the eslicarbazepine has a particle size distribution $D_{90}$ between 5 μm and 200 μm, wherein the composition is prepared using dry granulation, wet granulation, blending, spheronization extrusion process, homogenization and/or hot melt extrusion processes.

5. The extended release powder for oral suspension of claim 1, wherein the extended release powder for oral suspension is provided in a kit comprising:
(a) an extended release suspension comprising eslicarbazepine acetate with one or more pharmaceutically acceptable excipients and/or carrier;
(b) a dispensing and/or dosing syringe or a measuring cup for administering the composition; and
(c) optionally, instructions for preparation and use.

6. An extended release suspension comprising the extended release powder for oral suspension of claim 1 and a carrier selected from aqueous and non-aqueous carriers.

7. The extended release suspension of claim 6, wherein the composition comprises eslicarbazepine acetate in an amount of from about 0.1 mg/mL to about 250 mg/mL of the suspension.

8. The extended release suspension of claim 6, wherein the pH of the suspension composition is in the range of about 3.0 to 8.0.

9. The extended release suspension of claim 6, wherein the suspension is free of polyoxyethylene stearate and xanthan gum.

10. The extended release suspension of claim 6, wherein the composition is characterized by having an in-vitro dissolution release profile using USP Type II (paddle) apparatus at 50 rpm, in 1000 mL, of acetate buffer with pH 4.5 at 37±0.5° C. as follows:
(a) not more than about 45% of eslicarbazepine is released after 4 hours, and
(b) not less than about 55% of eslicarbazepine is released after 12 hours.

11. An oral pharmaceutical extended release powder for suspension free of xanthan gum and polyoxyethylene stearate comprising cores and one or more pharmaceutically acceptable excipients external to the cores:
(i) the cores comprise:
(a) 0.1% to 15% by weight of eslicarbazepine acetate;
(b) 0.1% to 10% by weight of co-processed microcrystalline cellulose and carboxymethyl cellulose sodium, hydroxypropylmethyl cellulose, and combinations thereof;
(c) about 0.1% by weight of polysorbate 80; and
(d) about 69% to 78% by weight of sucrose;
(ii) a coating layer over said core comprising 0.1% to 10% by weight of ethyl cellulose, hydroxypropylmethyl cellulose, and combinations thereof; and
(iii) optionally one or more flavours,
wherein the pH of the composition is in the range of about 6.0 to 7.5 and the composition is characterized by having an in-vitro dissolution release profile of not less than about 55% of eslicarbazepine acetate is released after 12 hours using USP Type II (paddle) apparatus at 50 rpm, in 1000 mL, of acetate buffer with pH 4.5 at 37±0.5° C.

12. An extended release suspension comprising the extended release powder for oral suspension of claim 11 and a carrier selected from aqueous and non-aqueous carriers, wherein the suspension is free of xanthan gum and polyoxyethylene stearate.

13. The extended release suspension of claim 12, wherein the suspension is characterized by having an in-vitro dissolution release profile using USP Type II (paddle) apparatus at 50 rpm, in 1000 mL, of acetate buffer with pH 4.5 at 37±0.5° C. as follows:
(a) not more than about 45% of eslicarbazepine is released after 4 hours, and
(b) not less than about 55% of eslicarbazepine is released after 12 hours.

14. An oral pharmaceutical extended release powder for suspension free of xanthan gum and polyoxyethylene stearate in the form of cores coated with an extended release coating, the coated cores consisting of:
i. eslicarbazepine acetate;
ii. hydroxypropylmethyl cellulose;
iii. sucrose;
iv. carboxymethyl cellulose sodium;
v. polysorbate 80;
vi. ethyl cellulose; and
vii. optionally one or more flavours,
wherein the pH of the composition is in the range of about 6.0 to 7.5 and the composition is characterized by having an in-vitro dissolution release profile of not less than about 55% of eslicarbazepine acetate is released after 12 hours using USP Type II (paddle) apparatus at 50 rpm, in 1000 mL, of acetate buffer with pH 4.5 at 37±0.5° C.

15. An extended release suspension comprising the extended release powder for oral suspension of claim 14 and a carrier selected from aqueous and non-aqueous carriers, wherein the suspension is free of xanthan gum and polyoxyethylene stearate.

16. The extended release suspension of claim 15, wherein the suspension is characterized by having an in-vitro dissolution release profile using USP Type II (paddle) apparatus at 50 rpm, in 1000 mL, of acetate buffer with pH 4.5 at 37±0.5° C. as follows:
(a) not more than about 45% of eslicarbazepine is released after 4 hours, and
(b) not less than about 55% of eslicarbazepine is released after 12 hours.

17. The oral pharmaceutical extended release powder for suspension of claim 14, wherein the coated cores consist of:
i. eslicarbazepine acetate present at about 11.5% w/w;

ii. hydroxypropylmethyl cellulose present at about 3.5% w/w;
iii. sucrose present at about 75% w/w;
iv. carboxymethyl cellulose sodium present at about 0.7% w/w;
v. polysorbate 80 present at about 0.1% w/w;
vi. ethyl cellulose present at about 9% w/w, and
viii. optionally one or more flavours present at about 0.5% w/w,
wherein the pH of the composition is in the range of about 6.0 to 7.5 and the composition is characterized by having an in-vitro dissolution release profile of not less than about 55% of eslicarbazepine acetate is released after 12 hours using USP Type II (paddle) apparatus at 50 rpm, in 1000 mL, of acetate buffer with pH 4.5 at 37±0.5° C.

18. An extended release suspension comprising the extended release powder for oral suspension of claim 17 and a carrier selected from aqueous and non-aqueous carriers, wherein the suspension is free of xanthan gum and polyoxyethylene stearate.

19. The extended release suspension of claim 18, wherein the suspension is characterized by having an in-vitro dissolution release profile using USP Type II (paddle) apparatus at 50 rpm, in 1000 mL, of acetate buffer with pH 4.5 at 37±0.5° C. as follows:
   (a) not more than about 45% of eslicarbazepine is released after 4 hours, and
   (b) not less than about 55% of eslicarbazepine is released after 12 hours.

* * * * *